(12) United States Patent
Schnitzer et al.

(10) Patent No.: US 6,737,516 B1
(45) Date of Patent: May 18, 2004

(54) IMMUNOISOLATION OF CAVEOLAE

(76) Inventors: Jan E. Schnitzer, 1475 Trabert Ransch Rd., Encinitas, CA (US) 92024; Philip Oh, 302 Island Ave., Apt. 204, San Diego, CA (US) 92101

( * ) Notice: Subject to any disclaimer, the term of this patent is extended or adjusted under 35 U.S.C. 154(b) by 0 days.

(21) Appl. No.: 09/208,195

(22) Filed: Dec. 9, 1998

(51) Int. Cl.$^7$ .................................................. A23J 1/00
(52) U.S. Cl. ...................................... 530/413; 436/538
(58) Field of Search ........................... 530/413; 436/538

(56) References Cited

U.S. PATENT DOCUMENTS

| | | | |
|---|---|---|---|
| 5,281,700 A | 1/1994 | Schnitzer et al. | ............ 530/412 |
| 5,776,770 A | 7/1998 | Schnitzer | ................. 435/317.1 |

OTHER PUBLICATIONS

Scherer et al. JBC vol. 272:46: 29337–29346 1997.*
Schnitzer, J.E., et al., "Seperation of Caveolae from Associated Microdomains of GPI–Anchored Proteins," *Science*, 269:1435–1439 (1985).
Stan, R. –V., et al., "Immunoisolation and Partial Characterization of Endothelial Plasmalemmal Vesicles (Caveolae)," *Mol. Biol. Cell* 8:595–605 (1997).
Smart, E.J., et al., "A detergent–free method for purifying caveolae membrane from tissue culture cells," *Proc. Natl. Acad. Sci. USA* 92:10104–10108 (1995).
Liu, J., et al., "Organized Endothelial Cell Surface Signal Transduction in Caveolae Distinct from Glycosylphosphatidylinositol–anchored Protein Microdomains," *J. Biol. Chem.* 272(11) : 7211–7222 (1997).
Oh, P. and Schnitzer, J.E., "Towards understanding the basics of purifying caveolae," Abstract and poster presented at the American Society of Cell Biology meeting held Dec. 13–17, 1997.
Anderson, R.G.W., "Caveolae: Where incoming and outgoing messengers meet," *Proc. Natl. Acad. Sci., USA* 90:10909–10913 (1993).
Jacobson, B.S., et al., "Isolation and partial characterization of the luminal plasmalemma of microvascular endothelium from rat lungs," *European J. Cell Biol.*, 58:296–306 (1992).

Lisanti, M.P., et al., "Caveolin Forms a Hetero–Oligomeric Protein Complex That Interacts with an Apical GPI–linked Protein: Implications for the Biogenesis of Caveolae," *J. of Cell Biology*, 123(3):595–604 (1993).
Lisanti, M.P., et al., "Characterization of Caveolin–rich membrane Domains Isolated from an Endothelial–rich Source: Implications for Human Disease," *J. of Cell Biol.*, 126(1):111–126 (1994).
Lisanti, M.P., et al., "Caveolae, caveolin and caveolin–rich membrane domains: a signalling hypothesis," *Trends in Cell Biol.*, 4:231–235 (1994).
Rothberg, K.G., et al., "Caveolin, a Protein Component of Caveolae Membrane Coats," *Cell* 68:673–682 (1992).
Schnitzer, J.E., et al., "Endothelial Caveolae Have the Molecular Transport Machinery for Vesicle Budding, Docking and Fusion Including VAMP, NSF, SNAP, Annexins, and GTPases," *J. of Biological Chem.*, 270(24) :14399–14404 (1995).
Schnitzer, J.E., et al., "Caveolae from luminal plasmalemma of rat lung endothelium: Microdomains enriched in caveolin, $Ca^{2+}$ –ATPase and inositol triphosphate receptor," *Proc. Natl. Acad. Sci. USA*, 92:1759–1763 (1995).
Schnitzer, J.E., et al., "NEM inhibits transcytosis, endocytosis, and capillary permeability: implication of caveolae fusion in endothelia," *Am. Physiological Soc.*, H48–H55 (1995).

* cited by examiner

*Primary Examiner*—Patrick J. Nolan
(74) *Attorney, Agent, or Firm*—Hamilton, Brook, Smith & Reynolds, P.C.

(57) ABSTRACT

Method of producing purified caveolae are described, in which a sample of interest comprising plasma membranes is subjected to an immunoisolation method in which the sample of interest is incubated with an antibody that is specific for caveolin and which binds to caveolin in its native (oligomeric) state, preferably for a brief time period, and caveolae that are bound to the antibody are separated from other materials in the sample of interest. Purified caveolae produced by the methods, and uses for the purified caveolae, are also described.

22 Claims, 2 Drawing Sheets

IMMUNOISOLATION OF CAVEOLAE

GOVERNMENT SUPPORT

This invention was supported, in whole or in part, by grant HL43278 and HL52766 from the National Institutes of Health. The Government has certain rights in the invention.

BACKGROUND OF THE INVENTION

Cholesterol and glycolipids self-associate in lipid bilayers to form organized compositional microdomains (Thompson, T. E., et al., *Annu. Rev. Biophys. Chem.* 14:361 (1985)). Glycosyl-phosphatidylinositol (GPI)-anchored proteins and other lipid-linked proteins may preferentially partition into glycolipid microdomains that are resistant to nonionic detergent solubilization (Schroeder, R., et al, *Proc. Natl. Acad. Sci. USA* 91:12130 (1994); Brown, D. A. and Rose, J. K., *Cell* 68:533 (1992); Letarte-Murhead, M. et al., *Biochem. J* 143:51 (1974); Hoessli, D. and Runger-Brandle, E., *Exp. Cell. Res.* 166:239 (1985); Hooper, N. M. and Turner, A. J., *Biochem. J.* 250:865 (1968); Sargiacomo, M. et al., *J. Cell. Biol.* 122:789 (1993); Lisanti, M. P. et al., *J. Cell. Biol.* 123:595 (1993)). GPI-anchored proteins appear to be sorted into glycolipid, detergent-resistant "rafts" in the trans-Golgi network for polarized delivery to the cell surface by smooth exocytotic carrier vesicles which are resistant to detergents and also contain caveolin (Brown, D. A. and Rose, J. K., *Cell* 68:533 (1992); Sargiacomo, M. et al, *J. Cell. Biol.* 122:789 (1993); Lisanti, M. P. et al., *J. Cell. Biol.* 123:595 (1993); Brown, D. et al, *Science* 245:1499 (1989); Simons, K. and van Meer, G., *Biochemistry* 27:6197 (1988); Garcia, M. et al., *J. Cell Sci* 104:1281 (1993); Kurzchalia, T. V. et al., *J.Cell Biol.* 118:1003 (1992); Dupree, P. et al., *EMBO J.* 12:1597 (1993); Hannan, L. A. et al., *J. Cell. Biol.* 120:353 (1993)). Caveolae are smooth membrane invaginations that are also resistant to detergent extraction; they exist on the surface of many different cell types, and are especially abundant in endothelium. Caveolae are apparently also rich in glycolipids, cholesterol, and caveolin (Kurzchalia, T. V. et al., *J. Cell Biol.* 118:1003 (1992); Schnitzer, J. E. et al., *Proc. Natl. Acad. Sci. USA* 92:1759 (1995)). Low-density, Triton-insoluble membranes are frequently equated with caveolae (Sargiacomo, M., et al., *J. Cell Biol.* 122:789 (1993); Lisanti, M. P. et al., *J. Cell. Biol.* 123:595 (1993); Chang, W.-J. et al., *J. Cell. Biol.* 126:127 (1994); Lisanti, M. P. et al., *J. Cell. Biol.* 126:111 (1994)), but recent work has shown they have a mixture of detergent-resistant microdomains (Schnitzer, J. E. et al., *Science* 269:1435–1439 (1995)). Characterization of caveolae shows that they are very enriched in caveolin; the glycolipid GM1; the plasmalemmal CA2+-dependent adenosine triphosphatase; and the inositol 1,4,5-triphosphate receptor; these four molecules have all been shown by independent means to reside on the cell surface almost exclusively in caveolae (Dupree, P., et al., *EMBO J.* 12:1597 (1993); Parton, R. G., *J. Histochem. Cytochem.* 42:155 (1994); Rothberg, K. G. et al., *Cell* 68:673 (1992); Montessano, R. et al., *Nature* 296:651 (1982); Fujimoto, T., *J. Cell. Biol.* 120:1147 91993)) and thus represent key markers of caveolae.

Caveolae have been implicated not only in signaling but also in transport via endocytosis, transcytosis, and potocytosis (Montessano, R. et al., *Nature* 296:651 (1982); Schnitzer, J. E., *Trends Cardiovasc. Med.* 3:124 (1993); Oh, P. et al., *J. Cell Biol.* 127:1217 (1994); Schnitzer, J. E. and Oh, P.,*J. Biol. Chem.* 269:6072 (1994); Schnitzer, J. E. et al., *Proc. Natl. Acad. Sci. USA* 92:1759–1763 (1995); Schnitzer, J. E. et al., *J. Biol. Chem.* 270:14399–14404 (1995); Millci, A. J. et al., *J. Cell Biol.* 105:2604 (1987); Anderson, R. G. W. et al., *Science* 265:410 (1992)). However, there is disagreement as to whether caveolae serve as signaling centers (see Liu, J. et al., *J. Biol. Chem* 272:7211–7222 (1997), Schnitzer, J. E. et al., *Mol. Biol. Cell* 5:75a (1994); Schnitzer, J. E. et al., *Proc. Natl. Acad. Sci. USA* 92:1759–1763 (1995); Schnitzer, J. E. et al., *J. Biol. Chem.* 270:14399–14404 (1995); contrast with Stan, R.-V. et al., *Mol. Biol. Cell* 8:595–605 (1997)). The exact physiological composition and functions of caveolae remain undefined.

SUMMARY OF THE INVENTION

The present invention is drawn to methods of producing purified caveolae, as well as the purified caveolae produced by the methods, and uses of the purified caveolae. In the methods, immunoisolation of caveolae is performed, using an antibody that is specific for caveolin and that is able to bind oligomerized caveolin found around intact caveolae. Immunoisolation can be performed on a wide variety of starting materials, including cells of interest, such as cultured cells or cells isolated from a tissue; a tissue itself; cell lysate; microsomes derived from cells or from tissue; or a sample of plasma membranes.

In one embodiment, the starting material can be subjected to membrane disruption method and/or a preliminary separation step prior to the immunoisolation. If such a separation step is performed, the separation is based on a physical characteristic of cell membranes (for example, density, size, or phase separation), in order to provide a starting material containing a concentrated amount of plasma membranes. The initial separated fractions (e.g., the lowest density fractions in a density separation) are then collected, and subjected to the immunoisolation method to separate caveolae from other materials in the initial fractions.

During the immunoisolation, a sample of interest (e.g., the starting material, sample of plasma membranes, or initial fractions) that comprises plasma membranes is incubated, preferably for a brief time period (e.g., for less than approximately 2 hours, preferably for approximately one hour or less), with the antibody that is specific for caveolin. Caveolae that are bound to the antibody are then separated from other materials in the sample of interest, thereby producing purified caveolae.

In a preferred embodiment, a sample of plasma membranes from cells of interest is used as the sample of interest. The sample of plasma membranes can be subjected to a membrane disruption method, such as sonication or shearing, to produce disrupted plasma membranes. If desired, the disrupted plasma membranes can then be subjected to separation based on a physical characteristic of the membrane, as described above. The resultant material is then subjected to the immunoisolation method to separate caveolae from other materials in the initial fractions.

The methods of the invention provide simplified, efficient means to produce purified caveolae, while minimizing contamination and avoiding loss of molecules that dissociated from caveolae with time. The caveolae produced by the methods more closely resemble caveolae in their native state; as the methods eliminate extended immunoisolation methods which would otherwise result in significant loss of various caveolae components as well as adsorption of non-specific proteins or contaminating membranes. The methods can be used to produce purified caveolae from a wide variety of cells or tissues, including not only endothelial cells and tissues, but also other (non-endothelial) cells and tissues, as well as cultured cells.

DETAILED DESCRIPTION OF THE INVENTION

Figure 1:
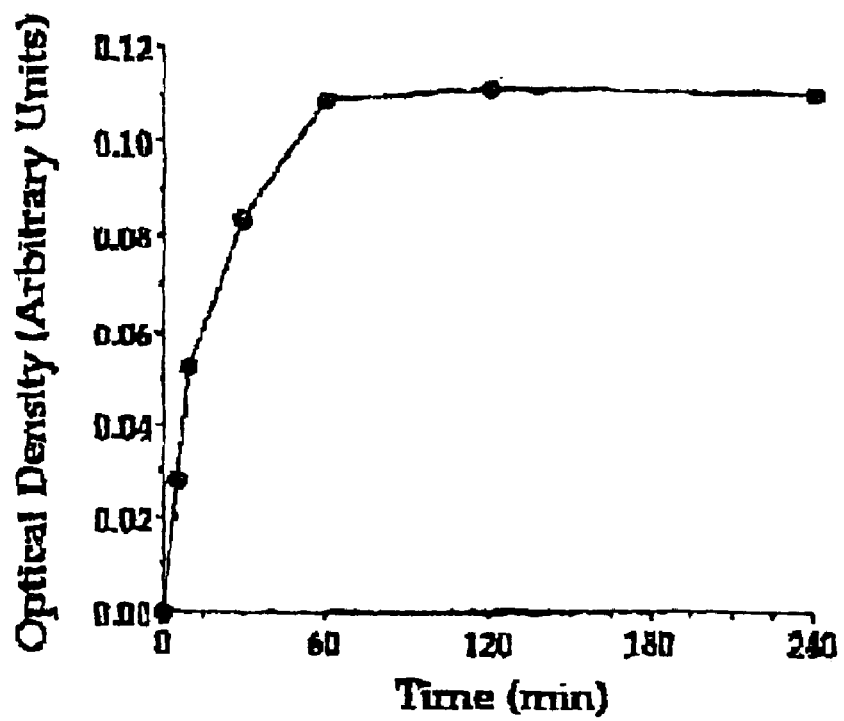
FIG. 1 is a graphic representation of the binding equilibrium over time of monoclonal antibody CAV to caveolin as it exists around caveolae in plasma membranes (i.e., in oligomerized form).

The present invention relates to purified caveolae, methods of producing the purified caveolae; and uses for the purified caveolae. As described herein, various techniques to isolate caveolae were compared to determine the effects of the techniques on the molecular composition of the final isolated caveolae. It was discovered that a brief immunoaffinity isolation procedure, using an antibody that was specific for caveolin and which bound with high affinity to caveolin in its native state as an oligomeric structure, allowed a simplified and quick isolation of caveolae. Caveolae isolated by this procedure retained more caveolae-related proteins than those isolated by other procedures, and thus were more representative of caveolae in their native state than caveolae isolated by other procedures.

As a result of this discovery, methods are now available to quickly and efficiently isolate caveolae. The methods can be carried out on any tissue, cell type, or cellular fraction whose plasma membranes contain the desired component (caveolae). For example, endothelial cells from representative tissues such as vascular, pulmonary, cardiac, cerebral, nephric, hepatic and endocrinous tissue, including the vascular system, lung, heart, liver, kidney, brain, and other organs, can be used. Alternatively, cells from any other type of tissue can be used, including non-endothelial cells. Cultured cells, cells isolated from a tissue, or a cell lysate can also be used, as can a tissue itself, as well as microsomes derived from cells or from a tissue. The tissue, cells, cell lysate, or microsomes from which the caveolae are isolated is referred to herein as the "starting material".

In the methods of the invention, a sample of interest (e.g., "starting material") that comprises plasma membranes is used. If desired, plasma membranes can first be separated from the other components of the tissue, cells, cell lysate, or microsomes used as the starting material, before immunoisolation is performed. A "sample of plasma membranes," as used herein, refers to plasma membranes that have been separated from other components of the starting material. The sample of plasma membranes can obtained from the starting material by any appropriate method, such as silica coating methods (see U.S. Pat. No. 5,281,700; Schnitzer, J. E. et al., *Proc. Natl. Acad. Sci. USA* 92:1759–1763 (1995); Schnitzer, J. E. et al., *J. Biol. Chem.* 270:14399–14404 (1995); Schnitzer, J. E. et al., *Science* 269:1435–1439 (1995); Schnitzer, J. E. et al., *Mol. Biol. Cell* 5:320(a) (1994); or Schnitzer, J. E. et al., *Mol. Biol. Cell* 5:75a (1994)), or density gradient centrifugation methods (see, e.g., Smart, E. J. et al., *Proc. Natl. Acad. Sci. USA* 92:10104–10108 (1995); *Biological Membranes: A Practical Approach* (Findlay and Evans, Eds., IRL Press at Oxford University Press, Oxford, England, 1987); *Subcellular Fractionation: A Practical Approach* (Graham and Rickwood, Eds., IRL Press at Oxford University Press, Oxford, England, 1997); *Cell Biology: A Laboratory Handbook* (J. Celis, Ed., 2$^{nd}$ Edition, Acad. Press, Inc., San Diego, Calif., USA, 1998), especially "Isolation and Subfractionation of Plasma Membranes to Purify Caveolae Separately from Glycol-phosphatidylinositol-anchored Protein Microdomains" (P. Oh and J. E. Schnitzer, pp. 34–45)). Alternatively, methods that utilize physiological release of caveolae by inducing budding from plasma membranes can be used to obtain the sample of plasma membranes (see, e.g., Schnitzer, J. E. et al., *Science* 274:239–242 (printer's erratun, *Science* 274:1069) (1996)).

If desired, the starting material comprising plasma membranes, or the sample of plasma membranes, can be subjected to a membrane disruption method, to produce a disrupted plasma membrane sample. The membrane disruption method can be sonication, shearing, or another appropriate membrane disruption method (see, e.g., *Biological Membranes: A Practical Approach* (Findlay and Evans, Eds., IRL Press at Oxford University Press, Oxford, England, 1987); *Subcellular Fractionation: A Practical Approach* (Graham and Rickwood, Eds., IRL Press at Oxford University Press. Oxford, England, 1997); *Cell Biology: A Laboratory Handbook* (J. Celis, Ed., 2$^{nd}$ Edition, Acad. Press, Inc., San Diego, Calif., USA, 1998)). The starting material, sample of plasma membranes, or disrupted plasma membrane sample, can also be subjected to a separation method based on a physical characteristic of the membranes, such as buoyant density, size, phase separation, to fractionate the sample. In a preferred method, the sample can be subjected to a separation method based on density. Representative separation methods based on density include sucrose density gradient centrifugation, and centrifugation using an Opti-Prep gradient (Gibco, Inc. (Grand Island, N.Y.). If a separation step is performed, it results in the production of fractions of components. Fractions which contain the greater amount of plasma membranes, with a lesser amount of contaminants, are isolated for further use. For example, separation based on density results in the production of fractions having different densities. Of these fractions, the initial fractions are collected. "Initial fractions," as used herein, refer to the top (i.e., the least dense) several fractions, that constitute approximately 10–25% of the fractions. In a preferred embodiment, the initial fractions constitute approximately 10–20% of the fractions. If the sample is fractionated based on another characteristic of the plasma membranes besides density, the appropriate fractions (i.e., the fractions that comprise the majority of the plasma membranes with minimal contamination from other components) are collected and used as the "initial fractions".

The starting material, sample of plasma membranes, disrupted plasma membrane sample, or the initial fractions are subjected to an immunoisolation method to isolate the purified caveolae. The terms, "immunoisolation" and "immuno-affinity isolation," used interchangeably herein, refer to separation of a component of interest (e.g., caveolae) from other materials using an antibody that is specific for (binds preferentially to) the component of interest. In immunoisolation, a sample of interest (i.e., the starting material, sample of plasma membranes, disrupted plasma membrane sample, or the initial fractions) that comprises plasma membranes is incubated with antibody that is specific for the component of interest; the component of interest, which is bound to the antibody that is specific for the component of interest, is then separated (isolated) from materials (components) that are not bound to the antibody. In a preferred embodiment of the invention, the incubation period of the immunoisolation method is a brief time, that is, the incubation is under about two hours, preferably about one hour or less. The brief time frame allows separation of purified caveolae that more closely resemble caveolae in their native state; as described in the Examples below. Extended immunoisolation results in significant loss of various caveolae components, including loss of the proteins eNOS and heterotrimeric G proteins into solution, and increases adsorption of nonspecific proteins and/or contaminating membranes.

In the immunoisolation method, an antibody that is specific for caveolin is used. The antibody that is specific for caveolin must be an antibody that binds preferentially to oligomeric caveolin, as caveolin is found in an oligomeric state surrounding intact caveolae (Scherer, P. E. et al., *J. Biol. Chem.* 272(46):29337–46 (1997)). In a preferred embodiment, the antibody binds to caveolin in its native state, and also binds to caveolin in its monomeric state (e.g., in a monomeric state such as after denaturation during Western blot analysis). The antibody allows separation of caveolae from other materials in the sample of interest. Caveolae that have been separated from other materials in the sample of interest are referred to herein as "purified caveolae". Purified caveolae can be bound to the antibody that is specific for caveolin, or can, if desired, be separated from the antibody.

Representative immunoisolation methods include isolation using the antibody specific for caveolin, where the antibody is coated on (attached) to a solid phase, such as beads or spheres. In a preferred embodiment, magnetic beads coated with the antibody are used. The materials that are bound to the antibody that is specific for caveolin (i.e., the purified caveolae), are separated from those materials in the sample of interest that are not bound to the antibody. For example, if a solid phase (e.g., magnetic beads) coated with antibodies is used for immunoisolation, the solid phase (e.g., the beads) together with materials bound to the antibodies that are coated with the solid phase (i.e., the purified caveolae), are separated from materials that are not bound to the solid phase. The purified caveolae can be released from the solid phase, if desired, using standard techniques.

The purified caveolae can be used for the identification of molecules and proteins which are involved in intra-, inter- or trans-cellular transport, in order to utilize such molecules and proteins for delivery of an agent (e.g., an antibody, a drug, a diagnostic agent or a gene) for treatment or therapy. Agents which target a particular component of caveolae may be more easily delivered to the cell and, if desired, into the cell, across one side of a cell to the other side (e.g., across a an endothelial cell layer). Thus, these molecules and proteins can be used to transport agents into and across cell membranes, such as into and/or across the endothelium and, as a result, across the endothelial barrier. The purified caveolae can also be used to target the endothelium, such as for delivery of an agent for treatment or therapy. Agents which target caveolae may also be more easily delivered to the cell and, if desired, into the cell, across one side of a cell to the other side (e.g., across a an endothelial cell layer). Thus, the caveolae can be used to transport agents into and across cell membranes, such as into and/or across the endothelium and, as a result, across the endothelial barrier. This is of considerable value because of the role the endothelium plays in many tissues of the body as a barrier to the passage of substances across the endothelium and into the underlying tissue. For example, agents (e.g., antibodies, drugs, diagnostic agents, genes) which bind to the caveolae or to particular components (e.g., molecules or proteins) can be used to target the caveolae. Alternatively, such agents can be used as transport agents, by conjugating another agent (e.g., a drug or a gene) to the agent which targets the caveolae.

The following Examples are offered for the purpose of illustrating the present invention and are not to be construed to limit the scope of this invention. The teachings of all references cited are hereby incorporated herein by reference.

EXAMPLE 1

Materials and Methods

Materials

Antibodies against caveolin (rabbit polyclonal and mouse monoclonal, clones #2297 and 2234, respectively) were purchased from Transduction Labs (Lexington, Ky.), or from Zymed (South San Francisco, Calif., mouse monoclonal #Z034). M-450 Dynabeads were purchased from Dynal (New Hyde Park, N.Y.). All other reagents and supplies were obtained as described previously (Schnitzer, J. E. et al., *J. Biol. Chem.* 270:14399–14404 (1995); Schnitzer, J. E. et al., *Science* 269:1435–1439 (1995); Schnitzer, J. E. et al., *Proc. Natl. Acad. Sci. USA* 92;1759–1764 (1995); Schnitzer, J. E. et al., *Science* 274:239–242 (printer's erratum, *Science* 274:1069) (1996)).

Western and Protein Analysis

The proteins of various tissue fractions were solubilized and separated by SDS-PAGE for direct analysis by silver staining or for Western analysis by electrotransfer to nitrocellulose filters followed by immunoblotting using enhanced chemiluminescence autoradiography and densitometric quantification using ImageQuant, as described previously (Schnitzer, J. E. et al., *J. Biol. Chem.* 270:14399–14404 (1995); Schnitzer, J. E. et al., *Science* 269:1435–1439 (1995); Schnitzer, J. E. et al., *Proc. Natl. Acad. Sci, USA* 92;1759–1764 (1995); Schnitzer, J. E. et al., *Science* 274:239–242 (printer's erratum, *Science* 274:1069) (1996)). Briefly, nitrocellulose filters from each gel were probed using primary antibody (dilution range from 1:1,000 to 1:5,000 in Blotto) followed by the appropriate HRP-labeled reporter antibodies (diluted 1:1,000). Sample protein concentrations were measured using the micro-BCA method with BSA as a standard.

Purification of Slilca-Coated Endothelial Cell Plasma Membranes and Caveolae

The luminal endothelial cell plasma membranes and caveolae were purified directly from rat lung tissue using an in situ silica-coating procedure as described previously ((Schnitzer, J. E. et al., *J. Biol. Chem.* 270:14399–14404 (1995); Schnitzer, J. E. et al., *Science* 269:1435–1439 (1995); Schnitzer, J. E. et al., *Proc. Natl. Acad. Sci. USA* 92;1759–1764 (1995)). Rat lung tissue was subfractionated to isolate first the luminal endothelial cell plasma membranes, and then to dislodge and isolate caveolae (Schnitzer, J. E. et al., *J. Biol. Chem.* 270:14399–14404 (1995); Schnitzer, J. E. et al., *Science* 269:1435–1439 (1995); Schnitzer, J. E. et al., *Proc. Natl. Acad. Sci. USA* 92;1759–1764 (1995)). The rat lung microvasculature was perfused in situ at 10–13° C. via the pulmonary artery with a solution of positively charged colloidal silica particles which coated the intimal endothelial cell surface membrane directly in contact with the circulating blood and created a stable silica pellicle that specifically marked this membrane and facilitated its purification from tissue homogenates by centrifugation. Electron microscopy showed that the sedimented pellets (P) contain silica-coated endothelial cell plasma membranes with many associated caveolae and little detectable contamination from other tissue components. Biochemically, P displayed ample enrichment for various endothelial cell surface markers relative to the starting whole lung homogenate (H) while excluding various other proteins found in intracellular organelles or other cell surfaces. The caveolae attached on the cytoplasmic side of the membranes opposite to the silica coating were stripped from these membranes by shearing during homogenization at 4° C. then, they were subjected to sucrose density centrifugation to yield a low buoyant density fraction of intact caveolae vesicles (V) well separated from the pellet containing resedimented silica-coated membranes stripped of the caveolae (P-V) and enriched in caveolae but not other markers. Alternatively, caveolae were separated from the plasma membranes (P) by sonication and then isolated in a low buoyant density fraction (referred to herein as PC) by sucrose density gradient centrifugation.

ELISA

The reactivity of caveolin antibodies with intact caveolae on the purified, silica-coated endothelial cell plasma membranes was assessed by ELISA. Briefly, equal aliquots of P (silica-coated luminal endothelial cell plasma membranes, isolated as described above) (5 µg in 100 µl) were placed in each well of a 96-well tray for drying overnight. After washing, the wells were blocked for 1 hour with EWB (2% ovalbumin and 2 mM $CaCl_2$ in PBS), incubated with EWB alone or EWB containing caveolin antibody, washed, incubated with reporter antibody conjugated to horseradish peroxidase (1:500 in EWB), and washed again. A substrate solution (50 mM $Na_2HPO_4$, 25 mM citric acid, 1.2 mg/ml of o-phenylenediamine dihydrochloride and 0.03% $H_2O_2$) was added and the reaction was stopped with 4 M $H_2SO_4$ before reading the signal using a Molecular Device Thermomax microplate reader.

Immuno-affinity Isolation of Caveolae

Magnetic immunoisolations were performed as follows: M450 DynaBeads conjugated with anti-mouse or -rabbit IgG were washed 3 times with PBS by resuspension and magnetic separation and then incubated for 4–8 hours with the desired antibody ($10^7$ M450 beads and 25 µg IgG). After washing 3 times with PBS, the beads were resuspended and incubated for one hour at 4° C. with various starting membrane subfractions (SM) before washing and magnetic separation to isolate two fractions: material bound to the beads (BS) and material not bound to the beads (UB). The SM, BD and fractions were subjected to SDS-PAGE and Western analysis. All experiments described herein were performed without added BSA as a blocker.

Simplified Purification of Caveolae from Plasma Membranes

Homogenates of tissue or cultured cells were subjected to Percoll gradient centrifugation to isolate the plasmalemmal fraction, in order to provide a sample enriched in plasma membranes. Lung tissue was homogenized in buffer (0.25 M sucrose/1 mM EDTA/20 mM Tricine, pH 7.8) and the lung homogenate was filtered sequentially through 53 and 30 µm Nytex filters. The cell/filtered tissue homogenates were subjected to centrifugation at 4° C. and the supernatant was saved. The resulting pellet was resuspended in 3 ml of buffer and subjected again to homogenization and centrifugation as above. The two supernatants were then combined and mixed with 30 ml of 30% Percoll in buffer. After centrifugation with a SW28 rotor at 84,000×g for 45 minutes at 4° C. (no brakes), a single membranous band was collected. The band was readily visible about ⅔ from the bottom of the tube. The band was pelleted by diluting the suspension 2–3 fold with MBS before centrifugation at 15,000×g at 4° C. for 2 hours. This band, referred to herein as the PM (plasma membrane) fraction, is enriched in plasma membranes.

To isolate the caveolae, the PM fraction was resuspended in 1 ml Mes-buffered saline (MBS) and sonicated on "high" (2×10 seconds; Branson sonicator), followed by immediate cooling on ice. The sonication procedure was repeated 3 times. The sonicated membranes were mixed with 50% Opti-Prep to yield a final concentration of 23% in a 3 ml total volume. After adding a continuous layer of 20–10% Opti-Prep to the SW 55 tube, the suspension was spun at 23,500×g for 90 minutes at 4° C. in a SW 55 rotor. Depending on the amount of PM loaded, 5–7 distinct membranous bands were visible. The first 2 bands (the "initial fraction"), or the top fourth of the tube, were then collected, and the membranes were pelleted by dilution and centrifugation as described above.

For immunoisolation of the caveolae, this membrane pellet was resuspended in 100 µl MBS for incubation with anti-mouse IgG Dynabeads (2×$10^7$ beads) prebound with 25 µg of CAV and processed as described above.

EXAMPLE 2

Characterization of an Antibody Reactive with the Caveolin Cage of Caveolae

Monoclonal antibody clone 2234(Transduction Labs, Lexington, Ky.), referred to herein as CAV, is not only specific for caveolin, but also binds caveolin in its native state as an oligomeric structural cave surrounding intact caveolae. Previous work (Scherer, P. E. et al., *J. Biol. Chem.* 270:16395–16401 (1995)) indicated that this antibody specifically binds the α-isoform of caveolin-1 via a specific epitope found in the N-terminal segment that is not present in the β-isoform.

Figure 2:
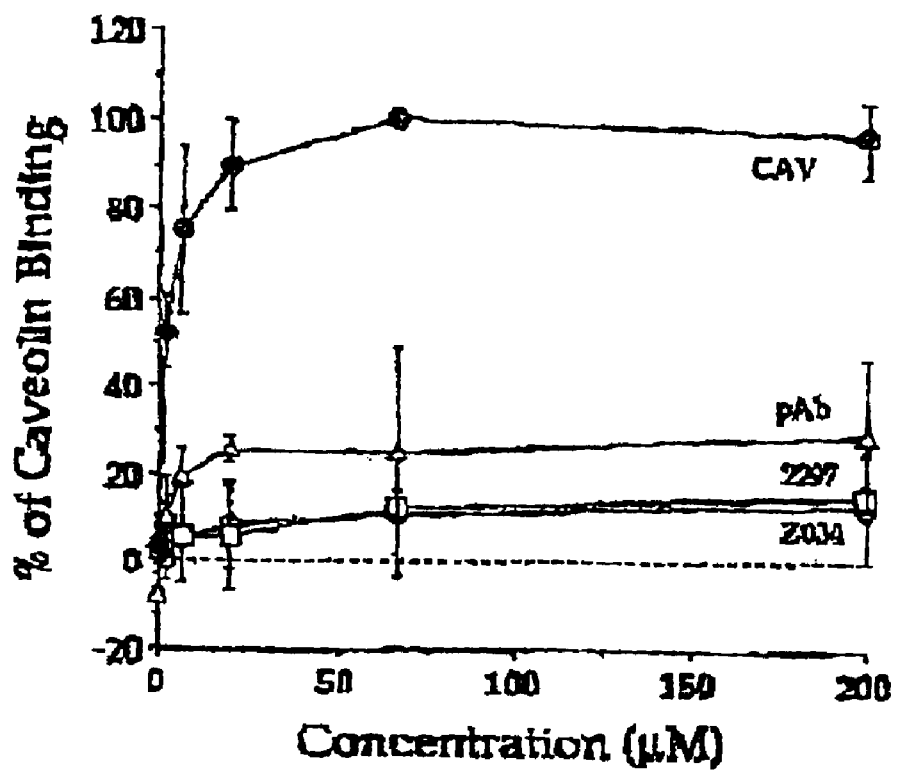
FIG. 2 is a graphic representation of the percent of binding of antibodies CAV, 2297 and Z034, as well as polyclonal antiserum pAB, to caveolin as it exists around caveolae in plasma membranes (i.e., in oligomerized form).

ELISA analysis, as described above, revealed that CAV was able to bind caveolin expressed on the purified silica-coated endothelial cell membranes (P); in addition, kinetic and binding analysis indicated rapid and high affinity binding of CAV to the caveolae in P. Titration of antibody concentration demonstrated that binding was saturable, with maximum binding occurring at about 10 nm. Time course studies revealed that binding equilibrium was achieved rapidly in just 1 hour (FIG. 1). Other monoclonal antibodies (2297 and Z034), also specific for caveolin by Western analysis, showed very little to no binding to caveolin in P by ELISA (FIG. 2). Polyclonal antibody showed a little reactivity, but only at higher concentrations and at levels insufficient to be useful for immunoisolation (FIG. 2).

The ability of CAV to react with fraction V (the low buoyant density fraction containing caveolae, isolated from P as described above) was then examined by performing immuno-affinity isolation of the caveolae as described above. Results indicated that CAV bound to intact caveolae in V, to allow immunoisolation. Greater than 95% of the caveolin in V was bound to the CAV-coated beads in the bound (BD) fraction, with little remaining behind in the unbound (UB) fraction. Furthermore, nearly all of the proteins detected in V fractionated to BD, rather than UB, upon CAV immunoisolation of the caveolae.

In contrast, other caveolin antibodies (2297, Z034) were ineffective, with nearly all of the caveolin and protein signal detected in UB rather than BD. The polyclonal antibody was poor, but partially effective. CAV thus appeared to be a high affinity antibody reacting quite rapidly and specifically with caveolin not only in its monomeric state after denaturation during Western analysis, but also in its native oligomeric state surrounding intact caveolae found in P and V.

EXAMPLE 3

Comparison of Sonication and Shearing for Isolation of Low Density Membranes

A comparison of the efficacy of sonication and of shearing in removing and isolating caveolae from the silica-coated cell plasma membranes (P) was performed, as described above. Sonication and shearing were both quite effective in not only removing caveolae from P (>80% loss in caveolin signal in the resedimented silica-coated membranes), but also yielding a caveolin-enriched, low density vesicular fraction after continuous sucrose density centrifuigation. Western blot analysis indicated that, relative to P, the V fraction (obtained by shearing) and the PC fraction (obtained by sonication) were both quite enriched in caveolin by more than 10-fold. Although PC and V had many proteins in common (eNOS, G proteins, annexin II and PKC), many other proteins found in P were readily detected in PC but not V, including the cytoskeletal protein $\beta$-actin, the GPI-anchored protein urokinase-plasminogen activator receptor (uPAR) and angiotensin converting enzyme (ACE). Neither $\epsilon$-COP (markedly depleted in P) nor the GPI-anchored 5'-nucleotidase (5'NT) (enriched in P) were apparent in V or PC. Thus, V was quite distinct in molecular composition from P and PC.

SDS-PAGE gels further confirmed the differences between the fractions: V had the simplest profile, with the fewest detectable proteins, whereas PC had many more protein bands than V but less than that seen in P. Although PC contained many, if not all, of the proteins apparent in V, it also contained many proteins found in P but not in V. This analysis indicated that sonication and shearing of P yielded vesicular fractions with the same low buoyant density but quite different molecular composition. It appeared that sonication of P released additional low density vesicles not found in V.

EXAMPLE 4

Immunoisolation from PC and V with CAV Antibody

The PC and V fractions described above were subjected to identical immunoaffinity isolation, as described above, for one hour using CAV bound to magnetic beads. The starting material (referred to as "SM"; SM here was either PC or V), the material not bound to the immuno-magnetic beads (UB) and the material bound to the beads (BD) were examined by Western blot analysis. The fractions were analyzed first to assess the relative distribution of the molecules by using equivalent volume conditions (the final volumes were equal in each fraction and the same volume of each fraction was added to the gel lanes, so that the same percentage or proportion of each fraction was analyzed).

Although ample signals for each of the assessed molecules were seen in the starting material SM (PC), only a subset of these molecules were found in BD, namely, the vesicles bound to the caveolin-antibody beads. Caveolin gave the strongest signal in BD relative to both UB and SM. PKC$\alpha$ and the G protein $G_{\alpha q}$, as well as to a lesser extent eNOS and $G_{\alpha s}$, were detected in BD, yet significant levels of each remained behind in UB. Little to no signal for annexin II, $\beta$-actin and uPAR was detected in BD; these proteins remained nearly completely in UB.

The results where fraction V was used as the starting material [SM (V)] differed significantly. In each case where a signal was present in SM (V), little to no signal was found in UB and nearly all of the signal was recovered in BD. For example, more than 95% of the signal in SM (V) for caveolin, G proteins, eNOS and PCK$\alpha$ was found in BD. uPAR and $\beta$-actin were not detected in any of these fractions. Thus, nearly all of the caveolin was accessible and able to interact with the immuno-beads, resulting in quantitative isolation of nearly all of the starting material. This is in contrast with the results when PC was used as the starting material, where a significant amount of caveolin was inaccessible to immunoisolation.

To be certain that proteins in PC, for which a mild to nil signal was detected in BD were not simply diluted out by maintaining equivalent volume conditions during the analysis, equal amounts of protein from each fraction were loaded onto the gels before Western analysis. This resulted in a signal for eNOS, G protein and annexin II that was more readily detected in BD from PC as the starting material. By contrast, little to no $\beta$-actin or uPAR was again detected in BD, with ample signal present in UB, consistent with these molecules not normally residing concentrated in caveolae. Analysis of fractions under volume vs. protein equivalence gave noticeably different results, revealing readily apparent differences between PC and V, as well as striking similarities between V and the immunobound fractions (UB) from both PC and V.

EXAMPLE 5

Immunopurification of Caveolae from Plasma Membrane Isolated without Silica Coating Rat lungs flushed free of blood were processed to isolate a plasma membrane fraction (PM) using Percoll gradient centrifugation, and then a caveolin-enriched fraction (AC) was isolated by sonication of PM followed by sucrose density centrifugation, as described by Smart et al. (Smart, E. J. et al., *Proc. Natl. Acad. Sci. USA* 92:10104–10108 (1995)). Western analysis was performed, revealing that PM was enriched in various plasmalemmal marker proteins including caveolin, 5'NT, $\beta$-actin, eNOS, and uPAR. PM also contained significant levels of $\epsilon$-COP, indicating the presence of contaminating Golgi and endosomal membranes. When PM was subfractionated as described by Smart et al. (supra) by sonication to produce small vesicles that were isolated by centrifugation, first as a broad band on a continuous sucrose gradient for separation, and then again on a step gradient effectively to concentrate the low density buoyant vesicles, the resulting AC fraction was quite enriched in caveolin and eNOS (>5-fold) which is consistent with past reports (Shaul, P. et al., *J. Biol. Chem.* 271:6518–6522 (1996)). It was also mildly enriched in $\beta$-actin and the GPI-anchored proteins 5'NT and uPAR, again consistent with past studies (Smart et al., supra). Although not enriched, molecules such as annexin II as well as $\epsilon$-COP were easily detected in the AC fraction. The proteins detected in silver-stained gels for AC and PM were similar but clearly not identical.

AC was also subjected to immunoisolation using the CAV antibody, as described above. Western analysis of the starting material SM (AC), as well as the UB and BD fractions, under equal protein conditions indicated that many proteins originally detected in AC did exist in the immunoisolated caveolin-coated vesicles (i.e., the caveolae), whereas many other proteins in starting material AC were not constituents of these vesicles. Caveolin in SM (AC) was found enriched in BD relative to UB. eNOS was clearly detected in BD with little signal in UB. Annexin II partitioned approximately equally between SM (AC), UB and BD. The GPI-anchored proteins 5'NT and uPAR, as well as the Golgi/endosomal marker $\epsilon$-COP and the cytoskeletal protein $\beta$-actin were not readily detected in BD, but rather, remained in UB. To be certain that the GPI-anchored proteins did not dissociate from membranes into solution, the UB fraction was subjected to centrifugation. It was found that the GPI-anchored proteins were in the membrane pellets. Thus, CAV immunoisolation purified the caveolin-coated caveolae in the AC fraction away from other membrane microdomains, including those rich in GPI-anchored proteins and/or cytoskeletal proteins.

EXAMPLE 6

CAV Immunoisolates Nearly All Proteins and Caveolae in V, but not PC or AC

The low density, caveolin-rich vesicles isolated from each fractionation procedure (V, PC and AC), were subjected identically to immunoisolation for one hour using CAV before performing SDS-PAGE as well as Western analysis for caveolin on the immuno-separated fractions. The gels revealed that nearly all of the membranes in V bound to the CAV beads, and that nearly all of the proteins as well as caveolin in V fractionated with the immuno-beads in BD, with little to none remaining in the UB fractions. Except for some bands coming from the IgG heavy and light chains, and BSA included by the manufacturer with the beads, the protein profile of V in SM was identical to BD. Conversely, when CAV was replaced with a clathrin antibody as a control, little to none of the proteins and caveolin originally in SM (V) was detected in BD but remained in UB.

For PC and AC, the results were strikingly different. Proteins were readily detected in both the BD and UB fractions, consistent with the presence of a significant population of low density vesicles that were not reactive with the caveolin antibody. Increasing the amount of antibody and immuno-beads several fold yielded the same result. The protein profiles in BD and UB were quite different, yet the proteins detected in BD from PC and AC were very similar to each other, as well as to those seen in V (also BD from V). Thus, subjecting the AC and PC fractions to immunoisolation revealed the existence of a heterogeneous population of distinct vesicles rather than a homogeneous population of caveolin-coated vesicles.

This analysis was in concordance with the Western analysis (above), that showed that many molecules in SM (PC) or SM (AC) were split between UB and BD, whereas for V, all molecules in SM (V) fractionated to BD with little to none remaining in UB. The same proteins detected in V (before immunoisolation as well as after) were found in the immunoisolated caveolae from PC and AC. These results indicated that V, but not AC nor PC, contained a homogeneous population of purified caveolin-coated caveolae. For PC and for AC, immunoisolation was a necessary additional step to purify caveolae. The caveolae immuno-purified from PC and AC appeared to be biochemically identical to each other as well as to those of V.

EXAMPLE 7

Time-dependent Translocation of eNOS into Solution

Overnight immuno-isolations, and 1 hour immunoisolations, were performed as described above in Example 6, to assess the ability of CAV antibody to isolate caveolae. Immunoblots of immunoseparated fractions indicated that although caveolin was almost completely detected in BD for both the 1 hour and overnight incubations, eNOS and $G_{as}$ were in BD in the 1 hour incubation, but largely absent from BD after the overnight incubation. Although it was clear that eNOS and $G_{as}$ were initially a part of the floating low density vesicles in V, the overnight incubation caused a substantial release of these signaling molecules from the caveolin-coated caveolae into solution. This apparent dissociation was confirmed in experiments performed in the absence of antibody, where a equal aliquots of P were placed in solution for times ranging from minutes to 16 hours, before sedimenting the membranes at 100,000×g and processing the nonparticulate supernatants and membrane pellets for Western analysis. As early as 2 to 4 hours, a loss in eNOS and $G_{as}$, but not caveolin, was detected from the pelleted membranes, with a concomitant gain in the supernatant. At 1 hour or less, all of the signal detected for these three proteins was detected in the membrane pellet. Thus, with time, these lipid-anchored signaling molecules dissociated from the membrane into solution.

EXAMPLE 8

Simplified Immunopurification of Caveolae From Plasma Membranes

A simplified approach to purifying caveolae from cells and tissues was developed. First, a plasma membrane-enriched fraction, equivalent to PM described above, was isolated from tissue and/or cell homogenates by standard centrifugation techniques (e.g., using Percoll gradients). This PM was subjected to vigorous sonication, and then loaded onto a continuous Opti-Prep gradient for centrifugation at 52,000×g for 90 min. The top 25% of the gradient (first 4 fractions) was collected. This caveolin-rich fraction, which contained much less ε-COP and GPI-anchored proteins than vesicles floating at higher densities, was then subjected to immunoisolation using CAV antibody.

This procedure yielded purified caveolin-coated caveolae equivalent in molecular composition to those derived by CAV immunoisolation of PC, V, and AC. This procedure shortened the procedure by avoiding the additional Opti-Prep centrifugation step as performed in the AC isolation.

Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of producing purified caveolae, comprising the step of subjecting a sample of interest comprising plasma membranes to an immunoisolation method to separate caveolae from other materials in the sample of interest, wherein the immunoisolation method comprises incubating the sample of interest with a monoclonal antibody that is specific for caveolin and which binds to oligomerized caveolin in its native state as an oligomeric structural cage surrounding intact caveolae, and separating caveolae that are bound to the antibody from other materials in the sample of interest, thereby producing purified caveolae.

2. The method of claim 1, wherein the sample of interest is selected from the group consisting of: cultured cells, cells isolated from a tissue, cell lysate, tissue, and microsomes derived from cells or from a tissue.

3. The method of claim 1, wherein the sample of interest is a sample of plasma membranes.

4. The method of claim 1, wherein the sample of interest is a disrupted plasma membrane sample.

5. The method of claim 1, wherein the sample of interest is initial fractions of staring material that has subjected to a separation method based on density.

6. The method of claim 1, wherein the antibody that is specific for caveolin is attached to a solid phase.

7. The method of claim 6, wherein the solid phase is magnetic beads.

8. The method of claim 1, wherein the immunoisolation method comprises incubating the sample of interest with an antibody that is specific for caveolin for a time period that is less than approximately 2 hours.

9. The method of claim 8, wherein the immunoisolation method comprises incubating the sample of interest with an antibody that is specific for caveolin for a time period that is equal to or less than approximately one hour.

10. A method of producing purified caveolae, comprising the steps of:
   providing a sample of interest comprising plasma membranes;
      a) subjecting the sample of interest to a membrane disruption method, thereby producing a disrupted plasma membrane sample;
      b) subjecting the disrupted plasma membrane sample to an immunoisolation method to separate caveolae from other materials in the disrupted plasma membrane sample, wherein the immunoisolation method comprises incubating the initial fractions with a monoclonal antibody that is specific for caveolin and which binds to oligomerized caveolin in it native state as an oligomeric structural cage surrounding intact caveolae, and separating caveolae that are bound to the antibody from the other materials in the disrupted plasma membrane sample,
   thereby producing purified caveolae.

11. The method of claim 10, wherein the membrane disruption method of step (b) is shearing.

12. The method of claim 10, wherein the membrane disruption method of step (b) is sonication.

13. The method of claim 10, wherein the antibody that is specific for caveolin is attached to a solid phase.

14. The method of claim 13, wherein the solid phase is magnetic beads.

15. The method of claim 10, wherein the immunoisolation method comprises incubating the disrupted plasma membrane sample with an antibody that is specific for caveolin for a time period that is less than approximately 2 hour.

16. The method of claim 15, wherein the immunoisolation method comprises incubating the disrupted plasma membrane sample with an antibody that is specific for caveolin for a time period that is equal to or less than approximately one hour.

17. A method of producing purified caveolae, comprising the steps of:
   a) providing a sample of interest comprising plasma membrane;
   b) subjecting the sample of interest to a membrane disruption method, thereby producing a disrupted plasma membrane sample;
   c) subjecting the disrupted plasma membrane sample to a separation method based on density, thereby producing fractions of the disrupted plasma membrane sample, and collecting initial fractions of the disrupted plasma membrane sample;
   d) subjecting tho initial fractions of the disrupted plasma membrane sample to an immunoisolation method to separate caveolae from the initial fractions, wherein the immunoisolation method comprises incubating the initial fractions with a monoclonal antibody that is specific for caveolin an which binds to oligomerized caveolin in its native state as an oligomeric structural cage surrounding intact caveolae, and separating caveolae that are bound to the antibody from other materials in the initial fractions,
   thereby producing purified caveolae.

18. The method of claim 17, wherein the separation method based on density of step (c) is sucrose density gradient centrifugation.

19. The method of claim 17, wherein the immunoisolation method comprises incubating the initial fractions with an antibody that is specific for caveolin for a time period that is less than approximately 2 hours.

20. The method of claim 19, wherein the immunoisolation method comprises incubating the initial fractions with an antibody that is specific for caveolin for a time period that is equal to or less than approximately one hour.

21. A method of producing purified caveolae, comprising the steps of:
   a) providing a sample of plasma membranes from cells of interest;
   b) subjecting the sample of plasma membranes to a membrane disruption method, thereby producing a disrupted plasma membrane sample;
   c) subjecting the disrupted plasma membrane sample to a separation method based on density, thereby producing fractions of the disrupted plasma membrane sample, and collecting initial fractions of the disrupted plasma membrane sample;
   d) subjecting the initial fractions of the disrupted plasma membrane sample to an immunoisolation method to separated caveolae from the initial fractions, wherein the immunoisolation method comprises incubating the initial fractions with a monoclonal antibody that is specific for caveolin and which binds to oligomerized caveolin in its native state as an oligomeric structural cage surrounding intact caveolae, for a time period that is less than approximately 2 hours, and separating caveolae that are bound to the antibody from other materials in the initial fractions,
   thereby producing purified caveolae.

22. The method of claim 21, wherein the immunoisolation method comprises incubating the initial fractions with an antibody that is specific for caveolin for a time period that is equal to or less than approximately one hour.

* * * * *